United States Patent [19]
Peterson et al.

[11] Patent Number: 5,691,328
[45] Date of Patent: Nov. 25, 1997

[54] PHOSPHOETHANOLAMINE CONJUGATES OF VITAMIN D COMPOUNDS

[75] Inventors: Andrew C. Peterson; Parvin T. Yazdi, both of Madison, Wis.

[73] Assignee: Clarion Pharmaceuticals Inc., Madison, Wis.

[21] Appl. No.: 703,447

[22] Filed: Aug. 27, 1996

Related U.S. Application Data

[60] Provisional application No. 60/011,078 Feb. 2, 1996.

[51] Int. Cl.$^6$ .................... A61K 31/59; C07C 401/00
[52] U.S. Cl. ............................................ 514/167; 552/653
[58] Field of Search ............................ 552/653; 514/167

[56] References Cited

U.S. PATENT DOCUMENTS

| | | | |
|---|---|---|---|
| 5,206,229 | 4/1993 | Calverley et al. | 514/167 |
| 5,225,579 | 7/1993 | Tahara | 552/653 |
| 5,342,833 | 8/1994 | Doran et al. | 514/167 |

OTHER PUBLICATIONS

Binderup, E.; Calverly, M.J., (1991) PCT Pat. Appl. No. WO91/00855.
Deluca, H.F.; Schnoes, H.K.; Perlman, K.L.; Kutner, A.; Brit. UK. Pat. Appl. GB 2,217,715 (01 Nov. 1989) U.S. Pat. Appl. 187,680 (29 Apr. 1988).
Deluca, H.F.; Schnoes, H.K.; Perlman, K.L., Brit. UK Pat. Appl. GB 2,217,716 (01 Nov. 1989, U.S. Pat. Appl. 187,615 (29 Apr. 1988)).
Schoenecker, B.; Reichenbaecher, M.; Giesling, S., Ger. Offen DE 4,334,154 (06 Apr. 1995).
Calverly, M.J., Tetrahedron (1987) 43(20):4609–4619.
Calverly, M.J., Trends Med. Chem. '90, Proc. Int. Symp. Med. Chem. 11th (1992), 299–306.
Kunkel, S.L., "Inflammatory Cytokines", pp. 1–15 in Manual of Vascular Mediators, P.A. Ward, Editor, produced by publishers of Hospital Practice.
Kutner, A. et al., (1986), Bioorganic Chemistry (1986) 14:134.
Murayama, E.; Muyamoto, H.; Kubodera, N.; Mori, T.; Matsunaga, I., Chem. Pharm. Bull. (1986) 34(10):4410–4413.
"Nomenclature of Vitamin D," Pure & Appl. Chem. (1982), 54(8):1511–1516.
Norman, A.W.; Schaefer, K.; Grigoluit, H.G.; Herrath, D.V. (Eds.) Proc. Workshop Vitam. D. 1988, 7th (Vitam. D) 1–78.
Norman, A.W.; Bouillon, R.; Thomasset, M., (Eds.) Proc. Workshop Vitam. D. 1991, 8th (Vitam. D) 127–217.
"Pharmacological Methods in the Control of Inflammation," Joseph Y. Chang and Alan J. Lewis (eds.) Alan R. Liss, Inc., New York, pp. 221–223.
Posner, G.; Dai, H.; Afarinkia, K.; Murthy, N.; Guyton, K.; Kensler, T., J. Org. Chem. (1993), 58:7209–7215.
Posner, G. and Johnson, N., J. Org. Chem. (1994), 59:7855–7861.
Ralph, W.C. and Nakoinz, I., "Antibody–Dependent Killing of Erythrocyte and Tumor Targets by Macrophage–Related Cell Lines: Enhancement by PPD and LPS.," J. Immunology (1977), 119:950–974.
Raschke, W.C.; Baird, S.; Ralph, P. and Nakoinz, I., "Functional Macrophage Cell Lines Transformed by Abelson Leukemia Virus," Cell (1978), 15:261–267.
Stamatov, S.D. and Gronowitz, S., Lipids (1990), 25(3):149–151.
Stork, G.; Hutchinson, D.; Okabe, M.; Parker, D.; Ra, C.; Ribereau, F.; Suzuki, T.; Zebovitz, T., Pure Appl. Chem. (1992), 64(12):1806–1812.
Taguchi, T.; Mitsuhashi, S.; Yamanouchi, A.; Kobayashi, Y.; Sai, H.; Ikekawa, N., Tetrahedron Lett. (1984), 25(43): 4933–4936.
M.A. Trush et al., "The Generation of Chemiluminescence by Phagocytic Cells," Methods in Enzymology (1978), 57:462–494.
Vitamin D Molecular, Cellular & Clinical Endocrinology, NY (1988).
Wolfgang, J., Synform (1985), 3(2):41–212.
Wolfgang, J., Synform (1986) 4(3):131–250.
Wolfgang, J., Synform (1987), 5(1):1–86.
S.H. Yuspa et al., Cancer Research (Dec. 1980), 40:4694–4703.
Stern, J., Internal Medicine, 4th edition, chapters 71–72, pp. 699–715, 1995.

Primary Examiner—Jose G. Dees
Assistant Examiner—Barbara Badio
Attorney, Agent, or Firm—DeWitt Ross & Stevens SC

[57] ABSTRACT

Certain phosphoethanolamine conjugates of vitamin D compounds are disclosed wherein the phosphoethanolamine moiety is bonded at the 3-position of the vitamin D moiety. The conjugates exhibit anti-tumor, anti-psoriatic and anti-inflammatory activities in addition to those activities associated with vitamin D. The invention embraces the novel compounds, pharmaceutical compositions thereof, and their methods of use.

23 Claims, 3 Drawing Sheets

PHOSPHOETHANOLAMINE CONJUGATES OF VITAMIN D COMPOUNDS

Priority is claimed to provisional patent application Ser. No. 60/011,078, filed Feb. 2, 1996.

FIELD OF THE INVENTION

The present invention relates to certain phosphoethanolamine conjugates of vitamin D compounds, pharmaceutically acceptable salts thereof, and to pharmaceutical compositions thereof. In addition to activities ascribed to vitamin D itself, the novel compounds herein described possess anti-tumor, anti-psoriatic and anti-inflammatory activities.

BACKGROUND OF THE INVENTION

Amidothiophosphates and glyceroamidothiophosphate derivatives of vitamin $D_3$ are known: S. D. Stamatov and S. Gronowitz, Lipids Vol. 25(3), pp. 149–151 (1990). Applicants are unaware of any phosphoethanolamine derivatives of vitamin D compounds.

It is known that sulfonylation will occur preferentially at the 3-hydroxy position when additional hydroxy groups are present at the 1, 24 or 25 positions of vitamin D derivatives: A. Kutner et al., Bioorganic Chemistry, Vol. 14, p. 134 (1986). This preferential occurrence is advantageously utilized in the analogous phosphorylation reaction hereinafter described to make the subject compounds.

DETAILED DESCRIPTION OF THE INVENTION

Figure 1:
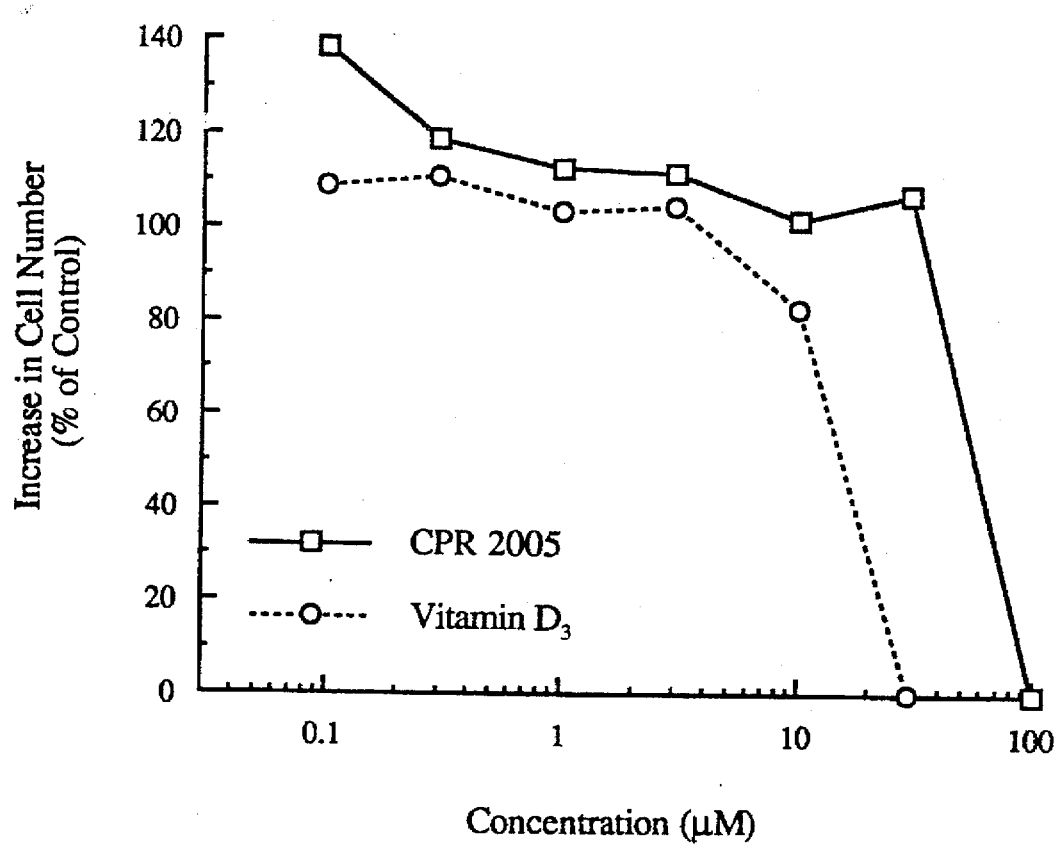
FIG. 1 is a graphical representation of results from an in vitro MDA-MB-231 Human Breast Cancer Cell inhibition assay of a compound of the invention, designated CPR 2005, in comparison with vitamin $D_3$.

The present invention relates to novel phosphoethanolamine conjugates of vitamin D compounds, natural or synthetic, as represented by the general formula (I):

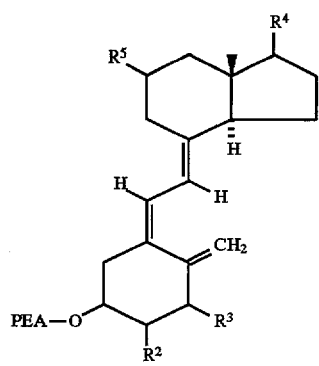

wherein:

PEA, together with the oxygen, bonded to both the PEA moiety and the vitamin D moiety, is phosphoethanolamine moiety of the formula:

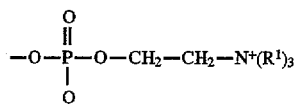

and wherein:

$R^1$ is hydrogen or methyl, provided that at least one $R^1$ is methyl;

$R^2$ represents hydrogen, methyl, carbonyl or halogen (F, Cl Br, I);

$R^3$ represents hydrogen or hydroxy;

$R^4$ represents a radical of the formula:

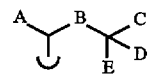

wherein:

A is hydrogen or methyl;

B is —$CH_2$—, —$CH_2CH_2$—, —$CH_2CH_2CH_2$—, —$OCH_2$—, —$OCH_2CH_2$—, —$OCH_2CH_2CH_2$—, —$CH_2OCH_2$—, —$CH_2OCH_2CH_2$—, —$CH_2OCH_2CH_2CH_2$—, —$CF_2$—, —$CF_2CF_2$—, —$CF_2CF_2CF_2$—, —CH=CH—, —C≡C—, —$CH_2$CH=CH—, —$CH_2CH_2$CH=CH—, —CH=CH$CH_2$—, —CH=CH$CH_2CH_2$—, —$CH_2$C≡C—, —CH=CH—CH=CH—, —CH=CH—CH=CH—CH=CH—, or —CH=CH—CH($CH_3$)—;

C and D, individually, are each hydrogen, $C_{1-3}$ alkyl, trifluoromethyl or cyclopropyl; C and D, together with the commonly bound carbon atom, is cyclopropyl; and E is hydrogen, methyl, methoxy, halogen (F, Cl, Br, I), trifluoromethoxy or, provided that either C or D is not hydrogen, hydroxy; and $R^5$ represents hydrogen, methyl, ethyl, halogen, vinyl, phenyl and halomethyl (halo=F, Cl, Br, I).

The formula (I) compounds may be alternatively denoted as "R-O-PEA", a vitamin D moiety conjugated at the 3-hydroxy position with the defined phosphoethanolamine moiety, wherein R represents the vitamin D moiety and -O-PEA represents the defined phosphoethanolamine moiety.

As known in the literature, there are several forms of Vitamin D, for example, vitamins $D_1$, $D_2$, $D_3$, and $D_4$. In addition to the chemical name for each form, trivial names for each have been reported. For example, cholecalciferol or calciol, also known as vitamin $D_3$, is chemically denoted as 9, 10-secocholesta-5,7,10(19)-trien-3-ol; calciferol, also known as vitamin $D_3$, is chemically denoted as 9,10-secoergosta-5,7,10(19), 22-tetraen-3-ol; and calcitriol, also known as 1α, 25-dihydroxyvitamin $D_3$, is chemically denoted as (1α, 3β, 5Z, 7E)-9,10-secocholesta-5,7,10(19)-triene-1,3,25-triol. As a result, attempts have been made by scientific entities to standardize the nomenclature; example, see "Nomenclature of Vitamin D", Pure & Appl. Chem., Vol. 54, No. 8, pp. 1511–1516, 1982. For purposes of this invention, "vitamin D" in the term "vitamin D compound" or "vitamin D moiety" is used in the same broad context as set forth in said reference, to wit:

"The term vitamin D should be used as a general term to describe all steroids that exhibit qualitatively the biological activity of calciol. The term should be used in derived terms such as vitamin D activity, vitamin D deficiency, vitamin D antagonist."

The moiety represented by R in formula (r) is derived from the corresponding vitamin D compound having a hydroxyl (—OH) in the 3-position, including all possible stereo isomeric and geometrically isomeric forms due to the asymmetric carbon atoms and the cis or trans configuration at double-bonds inherent in the vitamin D structure. Said vitamin D compounds with a hydroxy in the 3-position constitute the starting materials (A) used in preparing the subject phosphoethanolamine conjugates of vitamin D. Representative starting materials are identified in the following Table 1.

Reference 6: Murayama, E.; Miyamoto,H.; Kubodera,N.; Mori, T.; Matsunaga, I. *Chem. Pharm. Bull.* 1986, Vol. 34 (10), pp. 4410–4413. Compound 6: (20R)—(4-Ethyl-4-hydroxyhexyloxy)-(1S, 3R)-dihydroxy-9,10-secopregna-5(Z), 7 (E), 10(19)-triene.

Reference 7: Binderup, E.; Calverly, M. J. (1991) PCT Pat. Appl. No. WO91/00855.

Compound 7: (20R)-(5-Ethyl-5-hydroxyhepta-1,3-dienyl)-(1S,3R)-dihydroxy-9,10-secopregna-(5Z), (7E), 10(19)-triene.

Due to the presence of the phosphoethanolamine moiety (—O—PEA), the invention also comprehends salts of the formula (I) compounds and all isomeric forms thereof. These salts include acid addition salts, such as, for example,

TABLE 1

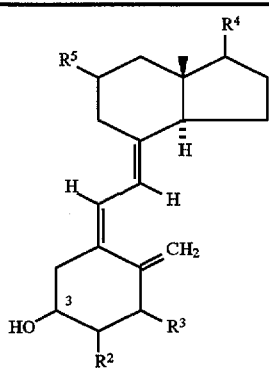

| Reference/ Compound | R² | R³ | R⁴ A | R⁴ B | R⁴ C | R⁴ D | R⁴ E | R⁵ |
|---|---|---|---|---|---|---|---|---|
| 1 | H | H | CH₃ | —CH₂CH₂CH₂— | CH₃ | CH₃ | H | H |
| 2 | H | H | CH₃ | —CH₂CH₂CH₂— | CH₃ | CH₃ | OH | H |
| 3 | H | OH | CH₃ | —CH₂CH₂CH₂— | CH₃ | CH₃ | OH | H |
| 4 | H | H | CH₃ | —CH=CH—CH(CH₃)— | CH₃ | CH₃ | H | H |
| 5 | H | OH | CH₃ | —CH=CH— | OH | cyclopropyl | H | H |
| 6 | H | OH | CH₃ | —OCH₂CH₂CH₂— | CH₃CH₂ | CH₃CH₂ | OH | H |
| 7 | H | OH | CH₃ | —CH=CH—CH=CH— | CH₃CH₂ | CH₃CH₂ | OH | H |

Reference 1: Wolfgang, J. *Synform* 1985, Vol. 3(2), pp. 41–212 and references cited therein.

Compound 1: (5Z,7E)-9,10-Seco-5,7,10(19)-cholestatrien-3-ol, also denoted herein as CPR 2005, see Example 1.

Reference 2: Wolfgang, J. *Synform* 1987, Vol. 5(1), pp. 1–86 and references cited therein.

Compound 2: (5Z,7E)-(3S)-9,10-Seco-5,7,10(19)-cholestatriene-3,25-diol.

Reference 3: Stork, G.; Hutchinson, D.; Okabe, M.; Parker, D.; Ra, C.; Ribereau, F.; Suzuki, T.; Zebovitz, T. *Pure Appl. Chem.* 1992, Vol. 64(12), pp. 1809–1812.

Compound 3: (5Z,7E)-(1S, 3R)-9,10-Seco-5,7,10(19)-cholestatriene-1,3,25-triol.

Reference 4: Wolfgang, J. *Synform* 1985, Vol. 3(2), pp. 41–122 and references cited therein.

Compound 4: (5Z,7E,22E)-(3S)-9,10-Seco-5,7,10(19),22-ergostatetraen-3-ol.

Reference 5: Calverly, M. J. *Tetrahedron* 1987, Vol. 43, pp. 4609–4619.

Compound 5: (5Z,7E ,22E,24S)-(1R,3S)-24-Cyclopropyl-9,10-secochola-5,7,10(19),22-tetraene-1,3, 24-triol.

those made with hydrochloric, hydrobromic, nitric, sulfuric, phosphoric, carbonic, acetic, citric or lactic acids. The salts may also include those made with bases, such as, for example, sodium hydroxide, potassium hydroxide or calcium hydroxide. The salts of the invention are made by conventional methods well known to the skilled. The salts for therapeutic use of the formula (I) compounds are pharmaceutically acceptable salts, as understood in the art.

I. CHEMISTRY

The compounds of the present invention (I) may be prepared by the one-step procedure outlined in the following Reaction Scheme. As used in the Reaction Scheme, the symbols R², R³, R⁴, R⁵ and PEA are as previously defined. The thus-obtained compounds in the Reaction Scheme may be purified by conventional methods of the art, e.g. chromatography, recrystallization, etc.

The compounds of formula (I) have asymmetric carbon atoms (C1, C3, C13, C14, C17, C20, and C25 positions in the secocholestatriene backbone) and in carbon atoms within R⁴ in their structure and consequently they may exist in the form of different stereo isomeric forms (diastereomers) or racemates. Substantially pure forms of each diastereomer, or of each enantiomer of a particular diastereomer, may be obtained, substantially free of the others by the application of art known resolution methodologies such as, for example, by selective crystallization or column chromatography, or by starting their preparation from the appropriate isomeric precursor.

In addition, cis and trans geometric isomers, when a double bond is present in the B portion of $R^4$, may also be present ha the subject compounds. Thus, by starting with the appropriate cis or trans precursor, the corresponding end product of formula (I) will be obtained.

All isomeric forms (i.e., stereo isomeric and geometrically isomeric forms and mixtures thereof) of the compounds of formula (I) are intended to be within the scope of this invention.

Working up the individual products indicated in the Reaction Scheme is advantageously carried out by standard methodologies, for example, by evaporating down the reaction solution or precipitating the product from the reaction solution by dilution with appropriate antisolvents. Particularly suitable methods for purifying the formula (I) compounds are the conventional chromatographic methods, such as preparative thin-layer chromatography (TLC), column chromatography, adsorption chromatography, medium pressure liquid chromatography (MPLC) or high pressure liquid chromatography (HPLC).

REACTION SCHEME

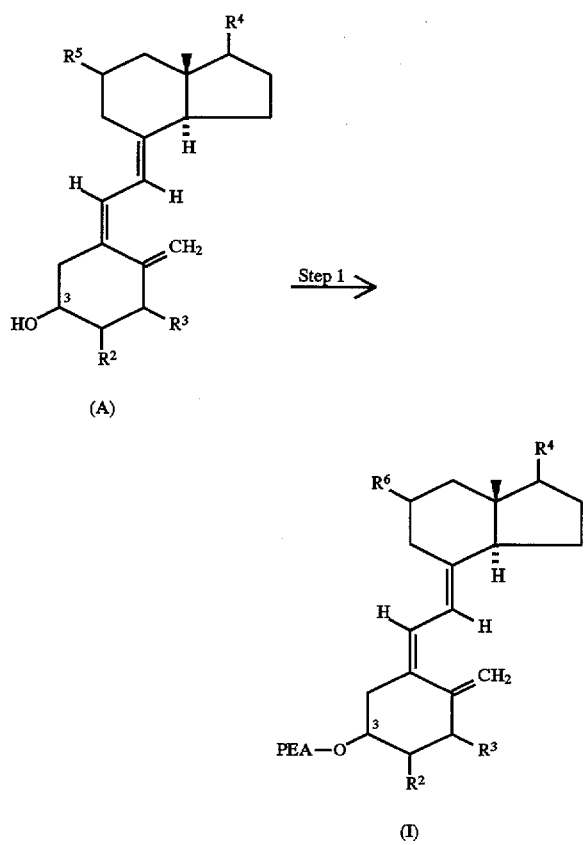

Step 1:

The compounds of formula (A) are known in the literature or are obtainable by art recognized procedures, for example, Wolfgang, J. Synform 1987, 3(2), 41–122;Wolfgang, J. Synform 1986, 4(3), 131–250; Wolfgang, J. Synform 1987, 5(1), 1–86; Stork, G., Hutchinson, D., Okabe, M., Parker, D., Choonsup, R., Ribereau, F, Suzuki, T., Zebovitz, T. Pure Appl. Chem. 1992, 64(12), 1806–1812; Posner, G, Johnson, N. J. Org. Chem. 1994, 59, 7855–7861; Posner, G., Dai, H., Afarinkia, K., Murthy, N.; Guyton, K., Kensler, T. J. Org. Chem. 1993, 58, 7209–7215; Calverly, M. J. Trends Med. Chem. '90, Proc. Int. Syrup. Med. Chem., 11th 1992, 299–306 and references cited therein. Deluca, H. F.; Schnoes, H. K.; Perlman, K. L.; Kutner, A. Brit. UK Pat. Appl. GB 2,217,715 (01 Nov., 1989), U.S. patent application Ser. No. 187,680 (29 Apr., 1988); Deluca, H. F.; Schnoes, H. K.; Perlman, K. L. Brit. UK Pat. Appl. GB 2,217,716 (01 Nov., 1, 1989, U.S. patent application Ser. No. 187,675 (29, Apr., 1988); Schoenecker, B., Reichenbaecher, M., Gliesling, S. Ger. Often. DE 4,334,154 (06 Apr., 1995); Taguchi, T.; Mitsuhashi, S.; Yamanouchi, A.; Kobayashi, Y.; Sai, H.; Ikekawa, N. Tetrahedron Lett. 1984, 25(43), 4933–4936; Calverly, M. J. Tetrahedron, 1987, 43(20), 4609–4619; Norman, A. W.; Bouillon, R.; Thomasset, M. (Eds) Proc. Workshop Vitam . D 1991, 8th (Vitam. D), 127–217 and references cited therein; Norman, A. W.; Schaefer, K.; Grigoleit, H. G.; Herrath, D. V. (Eds) Proc. Workshop Vitam. D 1988, 7th (Nitam. D), 1–78 and references cited therein.

The phosphoethanolamine moiety (PEA) is introduced into Compound (A) by the selective reaction of the 3-hydroxyl group in Compound (A) with 2-chloro-2-oxo-1, 3,2-dioxaphospholane in an inert organic aprotic solvent, such as, for example, toluene (preferred), benzene, chloroform, diethyl ether, dioxane and the like, followed by reaction with an appropriate amine $N(R^1)_3$, to yield the desired compound (I).

II. UTILITY

The compounds of the subject invention (I) and pharmaceutically acceptable salts thereof are useful chemopreventative and adjuvant agents in several aspects. They are advantageously administered to ameliorate conditions associated with vitamin D deficiency, for example, rickets in children and osteomalacia in adults. In addition, they are useful for the treatment of cancerous tumors and also for treating inflammation and hyperproliferative skin diseases such as psoriasis. The subject compounds may be used alone for such indications or in combination with other compatible medicaments.

A. ANTI-TUMOR

The following testing procedure, using the identified human breast and human colon carcinoma cell lines in an in vitro assay, demonstrates the marked anti-tumor (or antineoplastic) activity of the subject compounds.

Assay
1. Human tumor cell lines, obtainable from the American Type Culture Collection (ATCC):
   a. MDA-MB-231 (ATCC HTB-26): an estrogen receptor negative human breast carcinoma cell line (attachment dependent); and
   b. HT-29 (ATCC HTB-38): a human colon caminoma cell line (attachment dependent).
Culture media:
   a. For cell line 1-a: Dulbecco's Modified Eagle's Medium (DMEM) plus 10% Fetal Bovine Serum (FBS); and
   b. For cell line 1-b: 1:1 DMEM and Ham's F-12 (DMEM/ F12) plus 10% FBS.

3. Standard protocol for culturing cell lines: in T-75 or T-150 flasks; 37° C.; 95% air, 5% $CO_2$; 100% humidity;
   a. Cell lines are passaged when approximately 80% confluent; with trypsin (1 mg/ml) and EDTA (1 μM in ca-MG free Hank's balanced salt solution); at a 1:4 to 1:5 split;
   b. All procedures are performed aseptically in a class II biological safety cabinet using standard BL-2 containment procedures. In order to prevent genetic drift in stock cell lines, fresh cultures are prepared at approximately monthly intervals with cells thawed from liquid nitrogen storage.

4. Methodology:
   a. After cell passage, count cells with a hemacytometer;
   b. Adjust cell concentration to approximately 5,000 cells per 100 μL;
   c. Pipette 100 μL cell suspension into each well of a standard 96-well microtiter phte;
   d. Preincubate 24 hours to allow cells to attach;
   e. Add test compound dissolved in phosphate buffered saline (PBS), or in DMSO for the comparative compound, vitamin $D_3$, for final concentration levels ranging from 0 to 100 μM;
   f. Adjust volume to 200 μL per well by adding culture media without FBS; and
   g. Incubate 48 hours under standard culture conditions and determine end point.

End Point:
   a. Remove media and add 100 μL per well of cold (4° C.) 10% (w/v) trichloroacetic acid (TCA) in water;
   b. After 1 hour at 4° C., remove TCA and rinse cells 5 times with tap water;
   c. Air-dry plates;
   d. Add 50 μL per well of 0.4% (w/v) sulforhodamine B (SRB) in 1% (v/v) acetic acid in water;
   e. After 30 minutes at room temperature, rinse cells 4 times with 1% (v/v) acetic acid in water to remove residual stain;
   f. Air-dry plates;
   g. Dissolve stain by adding 100 μL per well of unbuffered Tris base, pH 10.5;
   h. Read absorbance at 562 nm using a standard 96-well microtiler plate reader. Absorbance readings are linear with dye concentrations below 1.8 absorbance units. To reduce absorbance, decrease wavelength at which measurements are taken;
   i. Data Analysis:
      single point reading: the higher the absorbance, the higher the cell amber;
      control—no test compound present in culture medium;
      background—no cell present, no test compound present in culture medium;
      initial control cell number (ICCN)—no test compound present in culture medium, end point was determined at the time of treatment;
      final control cell number (FCCN)—no test compound present in culture medium, end point was determined at 72 hours after treatment;
      final cell number (FCN)—test compound present in culture medium, end point was determined at 48 hours after treatment;
      calculate:
         ICCN=A(control, zero hour)-A(Background)
         FCCN=A(control, 48 hours)-A(Background)
         FCN=A(test compound, 48 hours)-A(Background)

$$\% \text{ Relative Increase in Cell Number} = \frac{FCN - ICCN}{FCCN - ICCN} \times 100$$

where A is absorbance.

Figure 2:
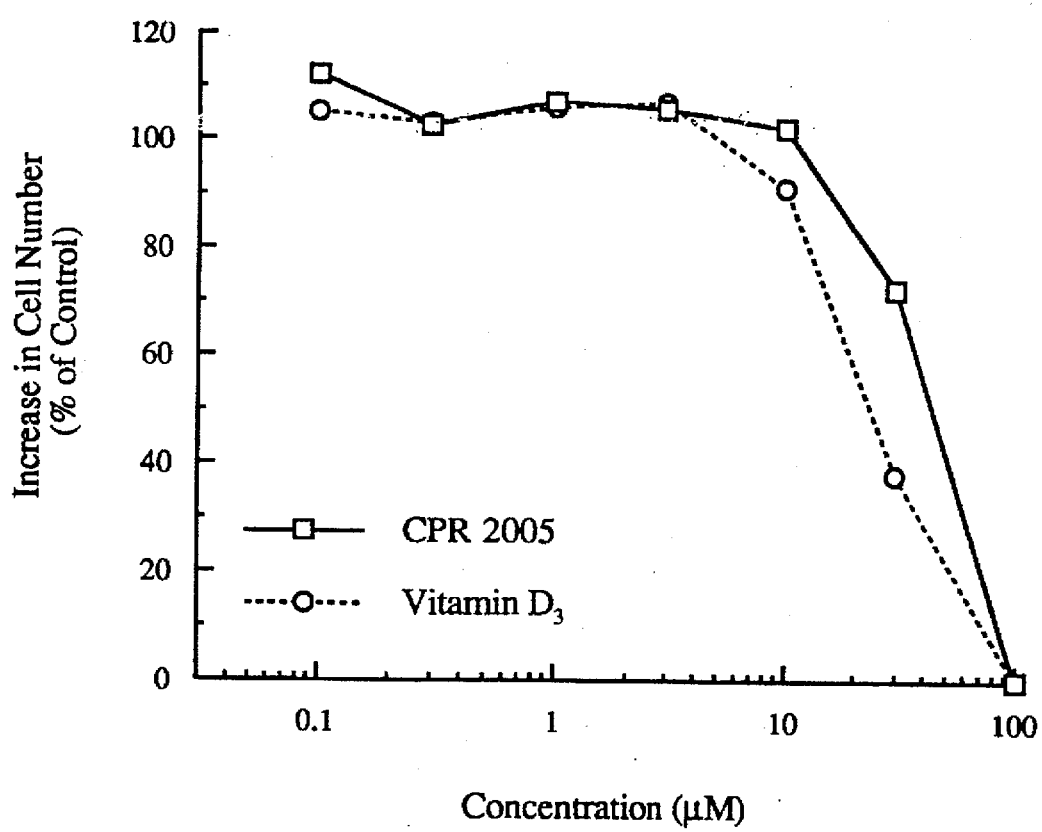
FIG. 2 is a graphical representation of results from an in vitro HT-29 Human Colon Cancer Cells inhibition assay of a compound of the invention, designated CPR 2005, in comparison with Vitamin $D_3$.

6. Results are represented in FIGS. 1 and 2, which illustrate the marked inhibition of MDA-MB-231 cell growth at 100 μM and HT-29 cell growth at concentrations above 30 μM by CPR 2005.

From the foregoing assay results, it is evident that the Formula (I) compounds demonstrate marked anti-tumor or anti-cancer activity, particularly against human breast and human colon carcinomas, as illustrated by the compound CPR-2005.

Anti-minor activity is to be expected against a wide spectrum of mammalian (including human) tumors and cancerous growths such as cancers of the oral cavity and pharynx (lip, tongue, mouth, pharynx), esophagus, stomach, small intestine, large intestine, rectum, liver and biliary passages, pancreas, larynx, lung, bone, connective tissue, skin, colon, breast, cervix, uteri, corpus endometrium, ovary, prostate, testes, bladder, kidney and other urinary tissues, eye, brain and central nervous system, thyroid and other endocrine glands, leukemias (lymphocytic, granulacytic, monocytic), Hodgkin's disease, non-Hodgkin's lymphomas, multiple myeloma, etc. Herein the terms "tumor", "cancer" and "caneerous growths" are used synonymously.

The instant invention thus provides a method of treating a tumor in a mammal afflicted with same comprising administering to said mammal an effective anti-tumor amount of a compound of Formula (I) or a pharmaceutically acceptable salt thereof. The invention also provides pharmaceutical compositions comprising an effective anti-tumor amount of a Formula (I) compound or such salt and a pharmaceutically acceptable carrier.

B. ANTI-PSORIASIS

Psoriasis is a chronic inflammatory dermatosis characterized, in part, by hyper-proliferation of keratinocytes and release of pro-inflammatory cytokines. Compounds that reduce hyperproliferation of keratinocytes in vitro are likely to have utility in the control of psoriasis. As will be shown, using the assay described below with the illustrative compound CPR-2005, the compounds of Formula (I) markedly inhibit proliferation of these cells in vitro, thus indicating that these compounds are useful in ameliorating psoriasis.

Assay
1. Cell line: PAM-212 murine keratinocyte cell line isolated and cultivated from newborn BALB/c mice (see S. H. Yuspa et al., Cancer Research, Vol. 40, pp. 4694–4703, December, 1980) that appears to retain many characteristics of normal keratinocytes.
2. Culture medium: 1:1 DMEM and Ham's F-12 with 10% FBS.
3. Culture conditions are the same as those described in part 3 of the assay protocol for anti-tumor activity.
4. Methodology is the same as that described in part 4 of the assay protocol for anti-tumor activity, except that, with reference to part 4(b) of the assay protocol for anti-tumor activity, cell concentration in this case is adjusted to 1,000 cells per 100 μL (rather than 5,000 cells per 100 μL).
5. End point determination and analysis are as described in part 5 of the assay protocol for anti-tumor activity.

Figure 3:
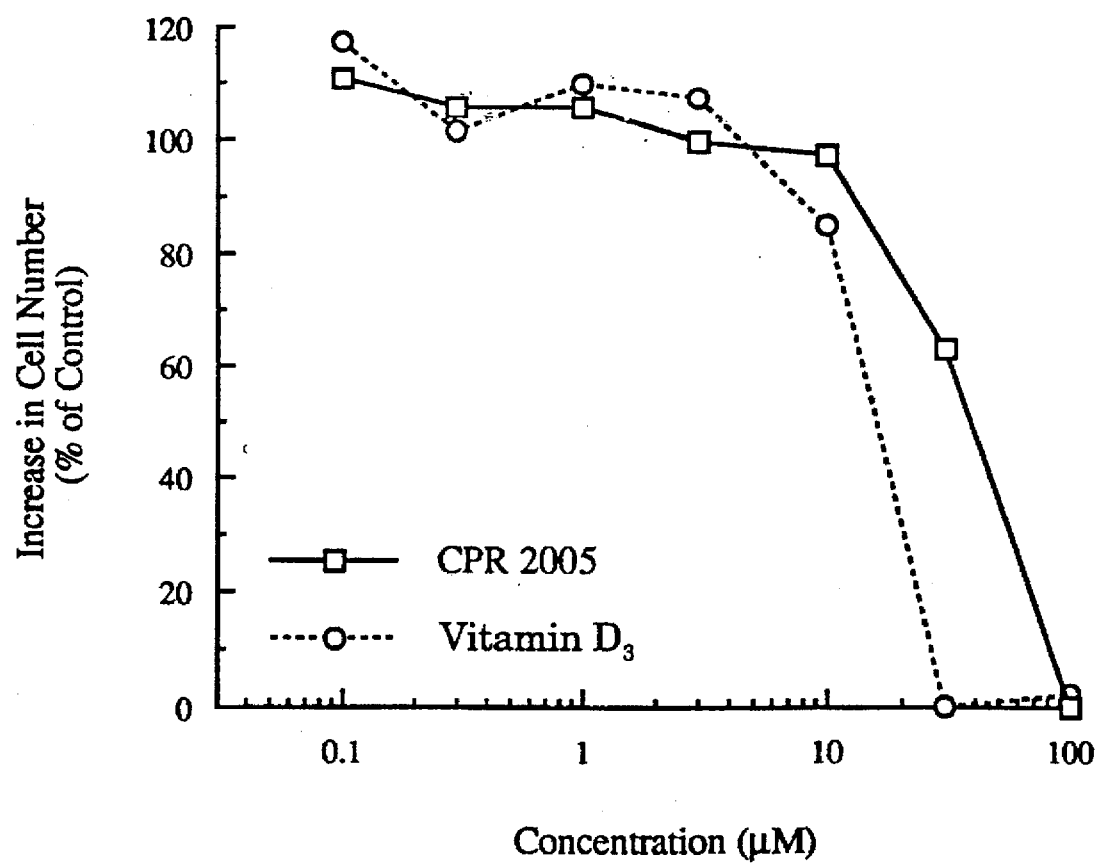
FIG. 3 is a graphical representation of results from an in vitro PAM-212 Mouse Keratinocytes inhibition assay of a compound of the invention, designated CPR 2005, in comparison with vitamin $D_3$.

Results are represented in FIG. 3, which illustrates the marked inhibition of keratinocyte proliferation, and consequently anti-psoriatic activity, at concentrations above 30 μM by CPR 2005.

The instant invention thus provides a method of treating psoriasis in a mammal inflicted with same comprising administering to said mammal an effective anti-psoriatic amount of a compound of Formula (I) or a pharmaceutically acceptable salt thereof. It also provides pharmaceutical compositions comprising an effective anti-psoriatic mount of a compound of Formula (I) or such salt and a pharmaceutically acceptable carrier.

C. ANTI-INFLAMMATORY

Inflammation is a complex process, involving a variety of cell types including macrophages, for example, see S. L. Kunkel, "Inflammatory Cytokines", pp. 1–15, in Manual of Vascular Mediators, P. A. Ward, Editor, produced by the publishers of Hospital Practice. References relative to macrophages are numerous, including, for example, J. Immunology Vol. 119, pp. 950–954 (1977) and Cell Vol. 15, pp. 261–267 (1978).

Macrophages are activated by infection and by a wide variety of non-infectious irritants and proinflammatory agents. Upon activation, macrophages participate in a variety of reactions. They may phagocytize bacteria and kill them by either oxygen-dependent or -independent pathways. With respect to the oxygen-dependent pathways, activation of macrophages induces them to increase oxygen consumption and produce reactive oxygen species (for example, radicals such as superoxide). Production of reactive oxygen species by activated macrophages is associated with inflammatory responses. In addition, on activation, macrophages release a variety of inflammatory cytokines, including several interleukins and tumor necrosis factor α (TNFα). Inhibition of any of these activation-related processes can lead to reduced inflammation.

For these reasons, macrophage activation is of critical importance in studies of the inflammatory process. Agents that reduce macrophage activation are likely to have utility as anti-inflammatory agents.

As will be shown, using the assay described below with the illustrative compound CPR 2005, the compounds of Formula (I) markedly reduce macrophage activation, thus indicating that these compounds are useful in ameliorating inflammation.

Assay for Anti-inflammatory Activity by Inhibition of Macrophage Chemiluminescence The RAW 264.7 cell line (available from the ATCC under accession no. TIB 71) is a murine monocyte/macrophage line the cells of which show many of the differentiative functions of a macrophage. Like macrophages, the cells are capable of phagocytosis and undergo an oxidative burst (increased oxygen consumption) and production of oxygen radicals (e.g., superoxide) in response to appropriate signals. Agents that inhibit the activation of these cells in vitro, so as to inhibit the respiratory burst and corresponding production of oxygen radicals associated with the activation, are therefore inhibitors of macrophage activation and critical steps in inflammatory processes.

The respiratory burst and corresponding production of oxygen radicals that accompany macrophage activation can be measured in a variety of ways, including chemiluminescence based on the reaction of the oxygen radicals with luminol added to the culture medium (see M. A. Trush et at., 1978, "The Generation of Chemiluminescence by Phagocytic Cells." Methods in Enzymology 57: 462–494). Indeed, chemiluminescence generated from luminol in the culture medium of macrophage cell lines is recognized in the art as a marker of macrophage activation.

1. Cell line: Raw 264.7 (ATCC TIB-71, attachment dependent);
2. Culture medium: DMEM with 10% FBS;
3. Standard protocol for culturing cell lines: in T-75 or T-150 flasks; 37° C.; 95% air, 5% $CO_2$; 100% humidity;
    a. Cell line is passaged when approximately 80% confluent; with trypsin (1 mg/ml) and EDTA (1 μM in ca-MG free Hank's balanced salt solution); at a 1:4 to 1:5 split;
    b. All procedures are performed aseptically in a class II biological safety cabinet using standard BL-2 containment procedures. In order to prevent genetic drift in stock cell lines, fresh cultures are prepared at approximately monthly intervals with cells thawed from liquid nitrogen storage.
4. Methodology:
    a. After cell passage, count cells with a hemacytometer;
    b. Adjust cell concentration to approximately 1,000,000 cells per mL;
    c. Suspend cells in DMEM lacking phenol red and without FBS;
    d. Pipette 1 mL of cell suspension into a standard luminometer cuvet (12×75), commercially obtainable from Analytical Luminescence Laboratories, San Diego, Calif., USA;
    e. Add luminol to final concentration of 0.2 μM;
    f. Add test compound dissolved in phosphate buffered saline (PBS), or in DMSO for the comparative compound, vitamin $D_3$, for final concentration levels ranging from 0 to 30 μM;
    g. Add 100 nanograms of phorbol myristate acetate (PMA); and
    h. Wait 1 minute and read photo counts (i.e., luminescence) on a Monolight 2010 luminometer available from Analytical Luminescence Laboratories, San Diego.
5. Data Analysis:

Background—no test compound present; no PMA present;

Control—no test compound present;

Calculate:

$$\% \text{ Inhibition} = \left( 1 - \frac{L(\text{test compound}) - L(\text{background})}{L(\text{control}) - L(\text{background})} \right) \times 100$$

where L is luminescence.

6. Results are represented in Table 1, which indicates the marked inhibition of luminescence by CPR 2005 at concentrations above 1 μM.

TABLE 1

Inhibition of Respiratory Burst
PMA-Stimulated Mouse Macrophages

| | % Inhibition | |
|---|---|---|
| Concentration (μM) | CPR 2005 | Vitamin $D_3$ |
| 30 | 99 | 12 |
| 10 | 98 | 2 |
| 3 | 90 | 9 |
| 1 | 45 | 10 |

In Vivo Assay

A common in vivo model for the evaluation of anti-inflammatory agents is PMA-induced inflammation in mouse ears. This method is described in "Pharmacological Methods in the Control of Inflammation", Joseph Y. Chang and Alan J. Lewis (eds), Alan R. Liss, Inc., N.Y., pp 221–223. In this assay, edema, which is a characteristic of inflammation, is quantified by determining ear thickness or ear weight approximately 6 hours after applying PMA to the ear.

1. Mice: Male CD-1, 21–24 g (Product Number 3002) obtainable from Harlan Sprague Dawley, Indianapolis, Ind., USA;
2. Methodology:
   a. Prepare 0.01% (w/v) PMA in a mixture of equal volumes of acetone and ethanol;
   b. Prepare 0.01% (w/v) PMA and 5% (w/v) test compound in a mixture of equal volumes of acetone and ethanol;
   c. Divide 9 mice into 3 groups of 3 mice each;
   d. Leave one group of mice untreated;
   e. Treat the second group of mice by applying 20 µL of PMA solution to both ears using a micropipetter;
   f. Treat the third group of mice by applying 20 µL of PMA solution to the right ear and 20 µL of PMA/test compound solution to the left ear;
   g. Wait 6 hours and euthanize the mice in a $CO_2$ chamber;
   h. Cut the ears and punch out circles of 6-mm diameter; and
   I. Measure the weight of three appropriate ear punches in the same group together.
3. Results are represented in Table 2, which shows the marked inhibition of PMA-induced inflammation in mouse ear by CPR 2005.

TABLE 2

PMA-Induced Inflammation in Ears of CD-1 Mice

| Treatment | Average Weight of Punched Ear (mg) | |
| --- | --- | --- |
| | left ear | right ear |
| Untreated (both ears) | 12 | 12 |
| PMA (both ears) | 34 | 28 |
| CPR 2005 + PMA (left ear), PMA (right ear) | 15 | 30 |

In view of their anti-inflammatory activity, the subject compounds are useful in the treatment of acute and chronic inflammatory diseases, such as, for example, dermatitis, conjunctivitis, bursitis, rheumatoid arthritis and the like.

The instant invention thus provides a method of treating inflammation in a mammal afflicted with same comprising administering to said mammal an effective anti-inflammatory amount of a compound of Formula (I) or a pharmaceutically acceptable salt thereof. It also provides pharmaceutical compositions containing an effective anti-inflammatory amount of a Formula (I) compound or such salt and a pharmaceutically acceptable carrier.

III. PHARMACEUTICAL COMPOSITIONS

Pharmaceutical compositions of the present invention, comprise an active compound, i.e., a Formula (I) compound or a pharmaceutically acceptable salt thereof, together with an acceptable carrier for it and optionally other therapeutically active ingredients. The carrier must be pharmaceutically acceptable in the sense of being compatible with the other ingredients of the composition and not deleterious to the recipient thereof.

The compositions include those suitable for oral, rectal or parenteral (including subcutaneous, intramuscular, intradermal and intravenous), nasal, or bronchial administration. Preferred are those suitable for oral or parenteral administration. Topical formulations are also included, for example, for anti-psoriatic usage.

It is noted that the Formula (I) compounds typically decompose on heating above 200° C. This characteristic may need to be taken into consideration in, for example, preparing tablets on a commercial scale where the heat of compression may be a factor. The Formula (I) compounds are also rather insoluble in water and, accordingly, liquid formulations which account for this factor may be made according to art-recognized pharmaceutical techniques. Examples of these techniques include an injection wherein the active compound is dissolved in a suitable solvent or co-solvent such as an appropriate polyethylene glycol, or a propylene glycol or the like; a sealed gelatin capsule enclosing an oily solution of the active compound; a suppository of the active compound in a conventional suppository base such as cocoa butter; or a liposome formulation, for example, the active compound and a glycerophospholipid such as phosphatidylcholine. In any event, the aforementioned characteristics of the Formula (I) compounds are not uncommon in the pharmaceutical area and, accordingly, art-recognized pharmaceutical techniques are employed to prepare appropriate formulations for such compounds as those of Formula (I) or pharmaceutically acceptable salts thereof.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid or solid carrier and then, if necessary, shaping the product into desired unit dosage form.

Formulations of the present invention suitable for oral administration may be presented as discrete units such as capsules, cachets, tablets, boluses or lozenges, each containing a predetermined amount of the active compound; as a powder or granules; or in liquid form, e.g., as suspension, solution, syrup, elixir, emulsion, dispersion, or the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

Formulations suitable for parenteral administration conveniently comprise a sterile preparation of the active compound in, for example, a polyethylene glycol 200 or propylene glycol solution which is preferably isotonic with the blood of the recipient.

Useful formulations also comprise concentrated solutions or solids containing the compound of Formula (I) which upon dilution with an appropriate solvent give a solution suitable for parenteral administration.

Preparations for topical or local applications, which are, for example, conventional for anti-psoriatic usage, comprise aerosol sprays, lotions, gels, ointments, etc. and pharmaceutically acceptable vehicles therefore such as, for example, lower aliphatic alcohols, polyglycerols such as glycerol, polyethyleneglycerol, esters of fatty acids, oils and fats, silicones, and other conventional topical carriers.

In topical formulations, the compounds of Formula (I) are preferably utilized at concentrations of from about 0.1% to about 5.0% percent by weight.

In addition to the aforementioned ingredients, the formulations of this invention may further include one or more optional accessory ingredients(s) utilized in the art of pharmaceutical formulations, e.g., diluents, buffers, flavoring agents, binders, surface active agents, thickeners, lubricants, suspending agents, preservatives (including antioxidants) and the like.

The compounds of Formula (I) and salts thereof of the invention are intended to be administered under the guidance of a physician or veterinarian.

The amount of compound of Formula (I) or salt thereof required to be effective for each of the herein indicated activities will, of course, vary with the individual mammal being treated and is ultimately at the discretion of the medical or veterinary practitioner. The factors to be considered include the condition being treated, the route of administration, the nature of the composition, the mammal's species and sex, the mammal's body weight, surface area, age and general condition, and the particular compound or salt to be administered. In general, the pharmaceutical compositions of this invention contain from about 0.5 to about 500 mg and, preferably, from about 5 to about 350 mg of the active ingredient, preferably in a unit dosage form, for each of the indicated activities.

A suitable effective dose is in the range of about 0.1 to about 200 mg/kg body weight per day, preferably in the range of about 1 to about 100 mg/kg per day, calculated as the non-salt form of Formula (I). The total daily dose may be given as a single dose, multiple doses, e.g., two to six times per day, or by intravenous infusion for a selected duration. Dosages above or below the range cited above are within the scope of the present invention and may be administered to the individual patient if desired and necessary.

For example, for a 75 kg mammal, a dose range would be about 7.5 to about 1500 mg per day, and a typical dose would be about 800 mg per day. If discrete multiple doses are indicated, treatment might typically be 200 mg of a compound of Formula (I) given 4 times per day.

Solutions of the subject compounds (I) in PBS have characteristics indicative of the presence of liposomes. These preparations require sonicatiou in order to form uniform, cloudy suspensions. The requirement for sonication and the cloudy appearance of the suspensions are some known properties of liposomal preparations. Additionally, foam generation, which is associated with micellar suspensions, is not a property of these preparations. Hence, unlike vitamin $D_3$, the subject compounds are capable of forming liposomes.

The following examples are intended to illustrate and not to limit the scope of the present invention.

EXAMPLE 1

(5Z,7E)-(3S)-9,10-Secocholesta-5,7,10(19)-trien-3-phosphocholine (CPR 2005).

Neat 4-chloro-2-oxo-1,3,2-dioxaphospholane (0.81 g, 5.72 mmol) is added in one portion to a stirred, mixture of (5Z,7E)-(3S)-9,10-secocholesta-5,7,10(19)-trien-3-ol (2.0 g, 5.2 mmol), commercially obtained from Spectrum Chemical Manufacturing Corp., Gardena, Calif., and triethylamine (0.84 mL, 5.76 mmol) in anhydrous toluene (80 mL) at room temperature under a nitrogen atmosphere. The resultant mixture is stirred at room temperature for four days. The white solid which precipitates is filtered off and washed with dry toluene. The toluene filtrate is concentrated in vacuo to leave a viscous residue which is further dried under high vacuum. Then, a mixture of trimethylamine (6.24 g) in acetonitrile (dried by distillation over phosphorus pentoxide, 65 mL) is added to the residue. The flask which contains the residue and trimethylamine in acetonitrile is sealed by tightly connecting glass stoppers with wire and is then heated with stirring to 60°–70° C. for 24 hours. Upon cooling, a white solid precipitates. The mixture is put into a refrigerator for 24 hours to further crystallize. The white solid is filtered from the cold solution and is washed sequentially with dry acetonitrile and then acetone. The product, (5Z,7E)-(3S)-9,10-secocholesta-5,7,10(19)-trien-3-phosphocholine, is purified by column chromatography on silica gel using 70:25:5 $CHCl_3$—$CH_3OH$—30% aqueous ammonia as the eluent. Recrystallization from ethanol-acetone followed by drying in vacuo gives 0.762 g (28.7% yield) of (5Z,7E)-(3S)-9,10-secocholesta-5,7,10(19)-trien-3-phosphocholine. TLC (silica gel 60): 65:35:5 CHCl3–$CH_3OH$–30% aqueous ammonia; $R_f$=0.47.

EXAMPLE 2

The procedure of Example 1 is followed, except that an equivalent amount of each vitamin D compound in Table 1, from 2 to 7, is used as the starting material to yield, as respective products, the corresponding 3-phosphocholine derivative of formula (I):

COMPOUND 2 (5Z,7E)-(3S)-9,10-Seco-5,7,10(19)-cholestatriene-25-ol-3-phosphocholine;

3 (5Z,7E)-(1S3R)-9,10-Seco-5,7,10(19)-cholestatriene-1,25-diol-3-phosphocholine;

4 (5Z,7E)-(3S)-9,10-Seco-5,7,10(19),22-ergostatetraen-3-phosphocholine;

5 (5Z,7E,22E,24S)-(1R,3S)-24-Cyclopropyl-9,10-secochola-5,7,10(19),22-tetraene-1,24-diol-3-phosphocholine;

6 (20R)-(4-Ethyl4-hydroxyhexyloxy)-(1S)-hydroxy-9,10-secopregna-(5Z),7(E), 10(19)-triene-(3R)-phosphocholine; and 7 (20R)-(5-Ethyl-5-hydroxyhepta-1,3-dienyl)-(1S)-hydroxy-9,10-secopregna-(5Z),(7E), 10(19)-triene-(3R)-phosphocholine.

EXAMPLE 3

By following the procedure of Example 1, except that an equivalent amount of the appropriate amine $N(R^1)_3$ is substituted for the trimethylamine used therein, the following are obtained as respective products;

(5Z,7E)-(3S)-9,10-secocholesta-5,7,10(19)-triene-3-phospho-(N-methyl)-ethanolamine; and (5Z,7E)-(3S)-9,10-secocholesta-5,7,10(19)-triene-3-phospho-(N,N-dimethyl)-ethanolamine.

EXAMPLE 4

Tablets

This is an illustrative example of tablets containing the following ingredients which may be prepared in conventional manner.

| Ingredient | Per Tablet (mg) |
|---|---|
| CPR-2005 | 50–100 |
| Lactose | 70 |
| Maize Starch | 70 |
| Polyvinylpyrrolidone | 5 |
| Magnesium stearate | 5 |
| Tablet Weight | 200–250 |

Oil-in-Water Cream Base Formulation:

This is an illustrative example of oil-in-water cream base formulation for topical use that may be prepared in a conventional manner using a Formula (I) compound as the active ingredient.

| Ingredient | Weight (g) |
|---|---|
| Active ingredient | 10.0 |
| Anhydrous lanolin | 20.0 |
| Polysorbate 60 | 4.0 |
| Sorbitan monopalmitate | 2.0 |
| Light liquid paraffin | 4.0 |
| Propylene glycol | 5.0 |
| Methyl hydroxybenzoate | 0.1 |
| Purified water | To 100.0 |

Capsules:

This is an illustrative example of capsules containing the following ingredients which may be prepared in a conventional manner:

| Ingredient | Per Capsule (mg) |
|---|---|
| CPR-2005 | 50 |
| Lactose | 450 |
| Magnesium Stearate | 5 |
| Capsule Weight | 505 |

What is claimed is:

1. A conjugate of a vitamin D moiety with a phosphoethanolamine moiety of formula

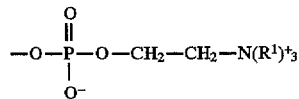

at the 3-position of the vitamin D moiety, wherein $R^1$ is hydrogen or methyl, provided that at least one $R^1$ is methyl, all isomeric forms of the conjugate, and pharmaceutically acceptable salts of the conjugate and all isomeric forms thereof.

2. A conjugate of claim 1 with the formula:

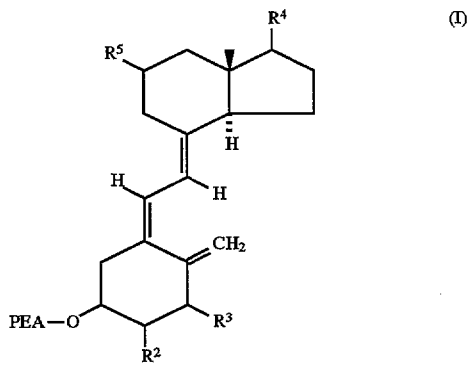

(I)

all isomeric forms thereof and pharmaceutically acceptable salts of the conjugate and all isomeric forms thereof, wherein -O-PEA represents a phosphoethanolamine of the fomula:

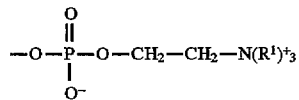

wherein:

$R^1$ is hydrogen or methyl, provided that at least one $R^1$ is methyl;

$R^2$ represents hydrogen, methyl, carbonyl or halogen;

$R^3$ represents hydrogen or hydroxy;

$R^4$ represents a radical of the formula:

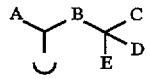

wherein:

A is hydrogen or methyl;

B is —CH$_2$—, —CH$_2$CH$_2$—, —CH$_2$CH$_2$CH$_2$—, —OCH$_2$—, —OCH$_2$OCH$_2$—, —OCH$_2$CH$_2$CH$_2$—, —CH$_2$OCH$_2$—, —CH$_2$OCH$_2$CH$_2$—, —CH$_2$OCH$_2$CH$_2$CH$_2$—, —CF$_2$—, —CF$_2$CF$_2$—, —CF$_2$CF$_2$CF$_2$—, —CH=CH—, —C≡C—, —CH$_2$CH=CH—, —CH$_2$CH$_2$CH=CH—, —CH=CHCH$_2$—, —CH=CHCH$_2$CH$_2$—, —CH$_2$C≡C—, —CH=CH—CH=CH—, —CH=CH—CH=CH—CH=CH—, or —CH=CH—CH(CH$_3$)—;

C and D, individually, are each hydrogen, C$_{1-3}$ alkyl, trifluoromethyl or cyclopropyl; C and D, together with the commonly bound carbon atom, is cyclopropyl; and E is hydrogen, methyl, methoxy, halogen, trifluoromethoxy or, provided that either C or D is not hydrogen, hydroxy; and $R^5$ represents hydrogen, methyl, ethyl, halogen, vinyl, phenyl or halomethyl.

3. A compound of claim 2 which is (5Z,7E)-(3S)-9,10-seco-cholesta-5,7,10(19)-trien-3-phosphocholine.

4. A compound of claim 2 selected from the group consisting of:

(5Z,7E)-(3S)-9,10-seco-5,7,10(19)-cholestatriene-25-ol-3-phosphocholine;

(5Z,7E)-(1S,3R)-9,10-seco-5,7,10(19)-cholestatriene-1,25-diol-3-phosphocholine;

(5Z,7E,22E)-(3S)-9,10-seco-5,7,10(19),22-ergostatetraen-3-phosphocholine;

(5Z,7E,22E,24S)-(1R,3S)-24-cyclopropyl-9,10-secochola-5,7,10(19),22-tetraene-1,24-diol-3-phosphocholine;

(20R)-(4-ethyl-4-hydroxyhexyloxy)-(1S)-hydroxy-9,10-secopregna-5(Z),7(E), 10(19)-triene-(3R)-phosphocholine;

(20R)-(5-ethyl-5-hydroxyhepta-1,3-dienyl)-(1S)-hydroxy-9,10-secopregna-(5Z),(7E), 10(19)-triene-(3R)-phosphocholine;

(5Z,7E)-(3S)-9,10-secocholesta-5,7,10(19)-triene-3-phospho-(N-methyl)-ethanolamine; and (5Z,7E)-(3S)-9,10-secocholesta-5,7,10(19)-triene-3-phospho-(N,N-dimethyl)-ethan-lamine.

5. A method of treating a solid tumor in a mammal afflicted with same which comprises administering to said mammal an anti-tumor effective amount of a conjugate of claim 1, any isomeric form thereof, or a pharmaceutically acceptable salt of the conjugate or isomeric form.

6. A method of claim 5 wherein the conjugate has the formula

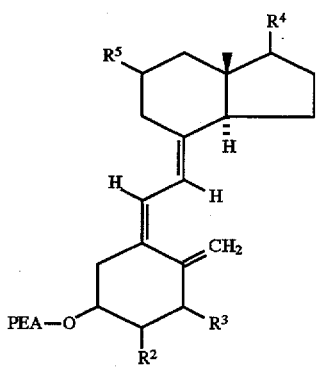

(I)

wherein:

-O-PEA represents a phosphoethanolamine of the formula:

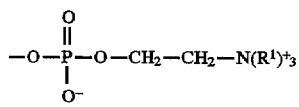

wherein:

$R^1$ is hydrogen or methyl, provided that at least one $R^1$ is methyl;

$R^2$ represents hydrogen, methyl, eaxbonyl or halogen;

$R^3$ represents hydrogen or hydroxy;

$R^4$ represents a radical of the formula:

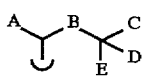

wherein:

A is hydrogen or methyl;

B is —CH$_2$—, —CH$_2$CH$_2$—, —CH$_2$CH$_2$CH$_2$—, —OCH$_2$—, —OCH$_2$CH$_2$—, —OCH$_2$CH$_2$CH$_2$—, —CH$_2$OCH$_2$—, —CH$_2$OCH$_2$CH$_2$—, —CH$_2$OCH$_2$CH$_2$CH$_2$—, —CF$_2$—, —CF$_2$CF$_2$—, —CF$_2$CF$_2$CF$_2$—, —CH=CH—, —C≡C—, —CH$_2$CH=CH—, —CH$_2$CH$_2$CH=CH—,
—CH=CHCH$_2$—, —CH=CHCH$_2$CH$_2$—, —CH$_2$C≡C—, —CH=CH—CH=CH—, —CH=CH—CH=CH—CH=CH—, or —CH=CH—CH(CH$_3$)—;

C and D, individually, are each hydrogen, $C_{1-3}$ alkyl, trifluoromethyl or cyclopropyl; C and D, together with the commonly bound carbon atom, is cyclopropyl; and E is hydrogen, methyl, methoxy, halogen, trifluoromethoxy or, provided that either C or D is not hydrogen, hydroxy; and $R^5$ represents hydrogen, methyl, ethyl, halogen, vinyl, phenyl or halomethyl.

7. The method of claim 6 wherein the conjugate is (5Z,7E)-(3S)-9,10-secocholesta-5,7,10(19)-trien-3-phosphocholine.

8. The method of claim 6 wherein the conjugate is selected from the group consisting of:

(5Z,7E)-(3S)-9,10-seco-5,7,10(19)-cholestatriene-25-ol-3-phosphocholine;

(5Z,7E)-(1S,3R)-9,10-seco-5,7,10(19)-cholestatriene-1, 25-diol-3-phosphocholine;

(5Z,7E,22E)-(3S)-9,10-seco-5,7,10(19),22-ergostatetraen-3-phosphocholine;

(5Z,7E,22E,24S)-(1R,3S)-24-cyclopropyl-9,10-secochola-5,7,10(19),22-tetraene-1,24-diol-3-phosphocholine;

(20R)-(4-ethyl-4-hydroxyhexyloxy)-(1S)-hydroxy-9,10-secopregna-5(Z),7(E), 10(19)-triene-(3R)-phosphocholine;

(20R)-(5-ethyl-5-hydroxyhepta-1,3-dienyl)-(1S)-hydroxy-9,10-secopregna-(5Z),(7E), 10(19)-triene-(3R)-phosphocholine;

(5Z,7E)-(3S)-9,10-secocholesta-5,7,10(19)-triene-3-phospho-(N-methyl)-ethanolamine; and (5Z,7E)-(3S)-9,10-secocholesta-5,7,10(19)-triene-3-phospho-(N,N-dimethyl)-ethanola mine.

9. A method of treating psoriasis in a mammal afflicted with same which comprises administering to said mammal an anti-psoriatic effective amount of a conjugate of claim 1, any isomeric form thereof, or a pharmaceutically acceptable salt of the conjugate or isomeric form.

10. A method of claim 9 wherein the conjugate has the formula:

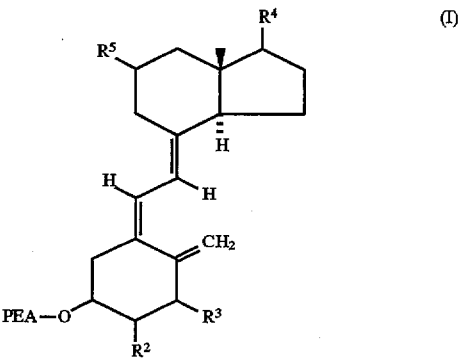

(I)

wherein:

-O-PEA represents a phosphoethanolamine of the formula:

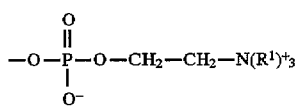

wherein:

R¹ is hydrogen or methyl, provided that at least one R¹ is methyl;

R² represents hydrogen, methyl, carbonyl or halogen;

R³ represents hydrogen or hydroxy;

R⁴ represents a radical of the formula:

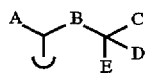

wherein:

A is hydrogen or methyl;

B is —CH₂—, —CH₂CH₂—, —CH₂CH₂CH₂—, —OCH₂—, —OCH₂CH₂—, —OCH₂CH₂CH₂—, —CH₂OCH₂—, —CH₂OCH₂CH₂—, —CH₂OCH₂CH₂CH₂—, —CF₂—, —CF₂CF₂—, —CF₂CF₂CF₂—, —CH=CH—, —C≡C—, —CH₂CH=CH—, —CH₂CH₂CH=CH—, —CH=CHCH₂—, —CH=CHCH₂CH₂—, —CH₂C≡C—, —CH=CH—CH=CH—, —CH=CH—CH=CH—CH=CH—, or —CH=CH—CH(CH₃)—;

C and D, individually, are each hydrogen, $C_{1-3}$ alkyl, trifluoromethyl or cyclopropyl; C and D, together with the commonly bound carbon atom, is cyclopropyl; and E is hydrogen, methyl, methoxy, halogen, trifluoromethoxy or, provided that either C or D is not hydrogen, hydroxy; and R⁵ represents hydrogen, methyl, ethyl, halogen, vinyl, phenyl or halomethyl.

11. The method of claim 10 wherein the conjugate is (5Z,7E)-(3S)-9,10-secocholesta-5,7,10(19)-trien-3-phosphocholine.

12. The method of claim 10 wherein the conjugate is selected from the group consisting of:

(5Z,7E)-(3S)-9,10-seco-5,7,10(19)-cholestatriene-25-ol-3-phosphocholine;

(5Z,7E)-(1S ,3R)-9,10-seco-5,7,10(19)-cholestatriene-1,25-diol-3-phosphocholine;

(5Z,7E,22E)-(3S)-9,10-seco-5,7,10(19),22-ergostatetraen-3-phosphocholine;

(5Z,7E,22E,24,S)-(1R,3S)-24-cyclopropyl-9,10-secochola-5,7,10(19),22-tetraene-1,24-diol-3-phosphocholine;

(20R)-(4-ethyl-4-hydroxyhexyloxy)-(1S)-hydroxy-9,10-secopregna-5(Z), 7(E), 10(19)-triene-(3R)-phosphocholine;

(20R)-(5-ethyl-5-hydroxyhepta-1,3-dienyl)-(1S)-hydroxy-9,10-secopregna-(5Z), (7E), 10(19)-triene-(3R)-phosphocholine;

(5Z,7E)-(3S)-9,10-secocholesta-5,7,10(19)-triene-3-phospho-(N-methyl)-ethanolamine; and (5Z,7E)-(3S)-9,10-secocholesta-5,7,10(19)-triene-3-phospho-(N,N-dimethyl)-ethanolamine.

13. A method of treating inflammation in a mammal afflicted with same which comprises administering to said mammal an anti-inflammatory effective amount of a conjugate of claim 1 any isomeric form thereof, or a pharmaceutically acceptable salt of the conjugate or isomeric form.

14. A method of claim 13 wherein the conjugate has the formula:

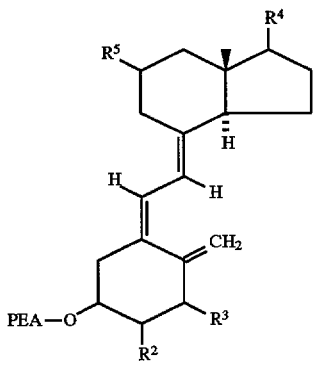

wherein:

-O-PEA represents a phosphoethanolamine of the formula:

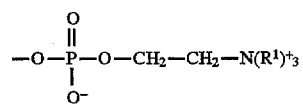

wherein:

R¹ is hydrogen or methyl, provided that at least one R¹ is methyl;

R² represents hydrogen, methyl, carbonyl or halogen;

R³ represents hydrogen or hydroxy;

R⁴ represents a radical of the formula:

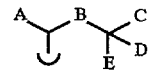

wherein:

A is hydrogen or methyl;

B is —CH₂—,—CH₂CH₂—, —CH₂CH₂CH₂—, —OCH₂—, —OCH₂CH₂—, —OCH₂CH₂CH₂—, —CH₂OCH₂—, —CH₂OCH₂CH₂—, —CH₂OCH₂CH₂CH₂—, —CF₂—, —CF₂CF₂—, —CF₂CF₂CF₂—, —CH=CH—, —C≡C—, —CH₂CH=CH—, —CH₂CH₂CH=CH—, —CH=CHCH₂—, —CH=CHCH₂CH₂—, —CH₂C≡C—, —CH=CH—CH=CH—, —CH=CH—CH=CH—CH=CH—, or —CH=CH—CH(CH₃)—;

C and D, individually, are each hydrogen, $C_{1-3}$ alkyl, trifluoromethyl or cyclopropyl; C and D, together with the commonly bound carbon atom, is cyclopropyl; and E is hydrogen, methyl, methoxy, halogen, trifluoromethoxy or, provided that either C or D is not hydrogen, hydroxy; and R⁵ represents hydrogen, methyl, ethyl, halogen, vinyl, phenyl or halomethyl.

15. The method of claim 14 wherein the conjugate is (5Z,7E)-(3S)-9,10-secocholesta-5,7,10(19)-trien-3-phosphocholine.

16. The method of claim 14 wherein the conjugate is selected from the group consisting of:

(5Z,7E)-(3S)-9,10-seco-5,7,10(19)-cholestatriene-25-ol-3-phosphocholine;

(5Z,7E)-(1S,3R)-9,10-seco-5,7,10(19)-cholestatriene-1,25-diol-3-phosphocholine;

(5Z,7E,22E)-(3S)-9,10-seco-5,7,10(19),22-ergostatetraen-3-phosphocholine;

(5Z,7E,22E,24S)-(1R,3S)-24-cyclopropyl-9,10-secochola-5,7,10(19),22-tetraene-1,24-diol-3-phosphocholine;

(20R)-(4-ethyl-4-hydroxyhexyloxy)-(1S)-hydroxy-9,10-secopregna-5(Z),7(E), 10(19)-triene-(3R)-phosphocholine;

(20R)-(5-ethyl-5-hydroxyhepta-1,3-dienyl)-(1S)-hydroxy-9,10-secopregna-(5Z),(7E), 10(19)-triene-(3R)-phosphocholine;

(5Z,7E)-(3S)-9,10-secocholesta-5,7,10(19)-triene-3-phospho-(N-methyl)-ethanolamine; and (5Z,7E)-(3S)-9,10-secocholesta-5,7,10(19)-triene-3-phospho-(N,N-dimethyl)-ethanola mine.

17. A pharmaceutical composition comprising an effective anti-minor effective, anti-psoriatic effective or anti-inflammatory effective amount of a conjugate of claim 1, any isomeric form thereof, or a pharmaceutically acceptable salt of the conjugate or isomeric form together with a pharmaceutically acceptable carrier.

18. A pharmaceutical composition according to claim 17 wherein the conjugate has the formula

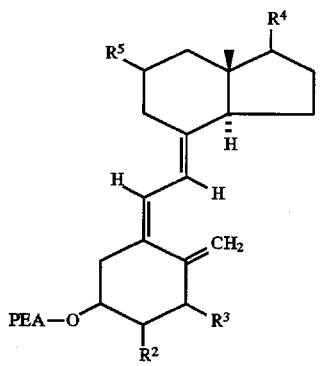

wherein:

-O-PEA represents a phosphoethanolamine of the formula:

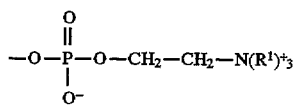

wherein:

$R^1$ is hydrogen or methyl, provided that at least one $R^1$ is methyl;

$R^2$ represents hydrogen, methyl, carbonyl or halogen;

$R^3$ represents hydrogen or hydroxy;

$R^4$ represents a radical of the formula:

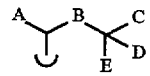

wherein:

A is hydrogen or methyl;

B is —CH$_2$—, —CH$_2$CH$_2$—, —CH$_2$CH$_2$CH$_2$—, —OCH$_2$—, —OCH$_2$CH$_2$—, —OCH$_2$CH$_2$CH$_2$—, —CH$_2$OCH$_2$—, —CH$_2$OCH$_2$CH$_2$—, —CH$_2$OCH$_2$CH$_2$CH$_2$—, —CF$_2$—, —CF$_2$CF$_2$—, —CF$_2$CF$_2$CF$_2$—, —CH=CH—, —C≡C—, —CH$_2$CH=CH$_2$—, —CH$_2$CH$_2$CH=CH—, —CH=CHCH$_2$—, —CH=CHCH$_2$CH$_2$—, —CH$_2$C≡C—, —CH=CH—CH=CH—, —CH=CH—CH=CH—CH=CH—, or —CH=CH—CH(CH$_3$)—;

C and D, individually, are each hydrogen, $C_{1-3}$ alkyl, trifluoromethyl or cyclopropyl; C and D, together with the commonly bund carbon atom, is cyclopropyl; and E is hydrogen, methyl, methoxy, halogen, trifluoromethoxy; or, provided that either C or D is not hydrogen, hydroxy; and $R^5$ represents hydrogen, methyl, ethyl, halogen, vinyl, phenyl or halomethyl, and a pharmaceutically acceptable carrier.

19. The composition of claim 18 wherein the conjugate is (5Z,7E)-(3S)-9,10-secocholesta-5,7,10(19)-trien-3-phosphocholine.

20. The composition of claim 18 wherein the conjugate is selected from the group consisting of:

(5Z,7E)-(3S)-9,10-seco-5,7,10(19)-cholestatriene-25-ol-3-phosphocholine;

(5Z,7E)-(1S,3R)-9,10-seco-5,7,10(19)-cholestatriene-1,25-diol-3-phosphocholine;

(5Z,7E,22E)-(3S)-9,10-seco-5,7,10(19),22-ergostatetraen-3-phosphocholine;

(5Z,7E,22E,24S)-(1R,3S)-24-cyclopropyl-9,10-secochola-5,7,10(19),22-tetraene-1,24-diol-3-phosphocholine;

(20R)-(4-ethyl-4-hydroxyhexyloxy)-(1S)-hydroxy-9,10-secopregna-5(Z),7(E), 10(19)-triene-(3R)-pbosphocholine;

(20R)-(5-ethyl-5-hydroxyhepta-1,3-dienyl)-(1S)-hydroxy-9,10-secopregna-5(Z),7(E), 10(19)-triene-(3R)-phosphocholine;

(5Z,7E)-(3S)-9,10-secocholesta-5,7,10(19)-triene-3-phospho-(N-methyl)-ethanolamine; and (5Z,7E)-(3S)-9,10-secocholesta-5,7,10(19)-triene-3-phospho-(N,N-dimethyl)-ethanola mine.

21. The composition of claim 18 in unit dosage form as a tablet or capsule containing from about 0.5 to about 500 mg of said conjugate.

22. The composition of claim 18 suitable for oral administration.

23. The composition of claim 18 suitable for topical administration.

* * * * *

UNITED STATES PATENT AND TRADEMARK OFFICE
CERTIFICATE OF CORRECTION

PATENT NO. : 5,691,328
DATED : November 25, 1997
INVENTOR(S) : Andrew C. Peterson and Parvin T. Yazdi It is certified that error appears in the above-identified patent and that said Letters Patent is hereby corrected as shown below:

On the title sheet, please delete the Abstract in its entirety and insert therefor the following abstract:

--The invention is drawn to conjugates of vitamin D compounds wherein a phosphoethanolamine moiety is bonded at the 3-position of the vitamin D moiety. The conjugates exhibit anti-tumor, anti-psoriatic and anti-inflammatory activities in addition to those activities associated with vitamin D. The invention embraces the novel compounds, pharmaceutical compositions thereof, and their methods of use.--

At column 2, lines 39-40, please delete "trifluoromethoxy or, provided that either C or D is not hydrogen, hydroxy" and insert therefor --trifluoromethoxy, or hydroxy, provided that when E is hydroxy, then either C or D is not hydrogen--.

At column 3, line 5, please delete "(r)" and insert therefor --(I)--.

In claim 2, column 16, line 54, please delete "and";
at lines 55-57, please delete "trifluoromethoxy or, provided that either C or D is not hydrogen, hydroxy", and insert therefor --trifluoromethoxy, or hydroxy, provided that when E is hydroxy, then either C or D is not hydrogen--.

In claim 5, column 17, lines 20 and 21, please delete ", any isomeric form thereof, or a pharmaceutically acceptable salt of the conjugate or isomeric form".

In claim 6, column 18, line 8, please delete "and";
at lines 9-11, please delete "trifluoromethoxy or, provided that either C or D is not hydrogen, hydroxy" and insert therefor --trifluoromethoxy, or hydroxy, provided that when E is hydroxy, then either C or D is not hydrogen--.

UNITED STATES PATENT AND TRADEMARK OFFICE
CERTIFICATE OF CORRECTION

PATENT NO. : 5,691,328
DATED : November 25, 1997
INVENTOR(S) : Andrew C. Peterson and Parvin T. Yazdi It is certified that error appears in the above-identified patent and that said Letters Patent is hereby corrected as shown below:

In claim 9, column 18, lines 45-46, please delete ", any isomeric form thereof, or a pharmaceutically acceptable salt of the conjugate or isomeric form".

In claim 10, column 19, line 35, please delete "and";
 at lines 36-38, please delete "trifluoromethoxy or, provided that either C or D is not hydrogen, hydroxy" and insert therefor --trifluoromethoxy, or hydroxy, provided that when E is hydroxy, then either C or D is not hydrogen--.

In claim 13, column 20, lines 2 and 3, please delete ",any isomeric form thereof, or a pharmaceutically acceptable salt of the conjugate or isomeric form".

In claim 14, column 20, line 57, please delete "and";
 at lines 58-60, please delete "trifluoromethoxy or, provided that either C or D is not hydrogen, hydroxy" and insert therefor --trifluoromethoxy, or hydroxy, provided that when E is hydroxy, then either C or D is not hydrogen--.

In claim 17, column 21, line 23, please delete "effective";
 at lines 26-29, please delete ", any isomeric form thereof, or a pharmaceutically acceptable salt of the conjugate or isomeric form together with". and insert --and--.

UNITED STATES PATENT AND TRADEMARK OFFICE
CERTIFICATE OF CORRECTION

PATENT NO. : 5,691,328

DATED : November 25, 1997

INVENTOR(S) : Andrew C. Peterson and Parvin T. Yazdi

It is certified that error appears in the above-identified patent and that said Letters Patent is hereby corrected as shown below:

In Claim 18, column 22, line 23, please delete "and";
    at lines 24-26, please delete "trifluoromethoxy; or, provided that either C or D is not hydrogen, hydroxy" and insert therefor --trifluoromethoxy, or hydroxy, provided that when E is hydroxy, then either C or D is not hydrogen--.

Signed and Sealed this

Tenth Day of March, 1998

*Attest:*

BRUCE LEHMAN

*Attesting Officer*     Commissioner of Patents and Trademarks